United States Patent [19]

Gast et al.

[11] Patent Number: 4,479,058
[45] Date of Patent: Oct. 23, 1984

[54] AUXILIARY UNIT FOR CARRYING OUT REFLECTION MEASUREMENTS USING AN IR SPECTROMETER

[75] Inventors: Jürgen Gast, Rheinstetten; Lutz Wunsch, Vökersbach; Günter Zachmann, Remchingen, all of Fed. Rep. of Germany

[73] Assignee: Bruker Analytische Messtechnik GmbH, Rheinstetten-Forchheim, Fed. Rep. of Germany

[21] Appl. No.: 426,221

[22] Filed: Sep. 28, 1982

[30] Foreign Application Priority Data

Dec. 2, 1981 [DE] Fed. Rep. of Germany ....... 3147689

[51] Int. Cl.$^3$ ............................................. G01J 5/08
[52] U.S. Cl. ................................... 250/343; 250/353; 356/73; 356/244
[58] Field of Search .................. 250/343, 353; 356/73, 356/244

[56] References Cited

U.S. PATENT DOCUMENTS 4,158,772 6/1979 Reedy ................................. 250/338

FOREIGN PATENT DOCUMENTS 1186241 9/1965 Fed. Rep. of Germany .
1497529 3/1969 Fed. Rep. of Germany .
2251080 5/1974 Fed. Rep. of Germany .

Primary Examiner—Janice A. Howell
Assistant Examiner—Constantine Hannaher
Attorney, Agent, or Firm—Burmeister, York, Palmatier, Hamby & Jones

[57] ABSTRACT

An auxiliary device enabling reflection measurements to be carried out by an IR spectrometer designed for the performance of transmission measurements comprises two deflecting mirrors (22, 23) to be positioned in the straight beam section of the spectrometer and two focussing reflector arrangements (26, 2, 27) of which the first forms at the location of the sample (16) to be investigated by the reflection method a reduced image of the focus (30) situated within the ray of beams (28) deflected by the first deflecting mirror (22) while the said second focussing reflector arrangement forms an enlarged image of the said reduced focus at a distance before the said second deflecting mirror (23) so that the beam of rays (33) emitted by the said second deflecting mirror forms a prolongation of the beam of rays inciding upon the said first deflecting mirror just as if the auxiliary device did not exist. Each reflector arrangement comprises a collimator mirror (26, 27) for parallelizing the divergent beam of rays emitted by the associated deflecting mirror (22, 23) and sections of a common parabolic mirror (2), the beams of rays (29, 31) emitted by the said collimator mirror (26, 27) extending in parallel to the axis of the said parabolic mirror (2) and the sample being arranged at a point coinciding with its focal point (16).

10 Claims, 6 Drawing Figures

AUXILIARY UNIT FOR CARRYING OUT REFLECTION MEASUREMENTS USING AN IR SPECTROMETER

Be it known that we, Jürgen Gast, Lutz Wunsch, and Günter Zachmann, all German nationals, having our respective residences at Ebersteinstrasse 39, 7512 Rheinstetten-3; Allmendstrasse 14, 7502 Völkersbach-3 and Hohensteinstrasse19, 7537 Remchinngen-1, all in West-Germany, have invented a new and useful auxiliary device for carrying out reflection measurements using an IR spectrometer designed for the performance of transmission measurements and comprising optical means for generating a beam of rays focussed in a cross-sectional plane located within a straight section and intended to receive the sample to be investigated by transmission, which auxiliary device comprises two deflecting mirrors to be positioned in the straight beam section on both sides of the cross-sectional plane and further two focussing reflector arrangements of which the first forms at the location of the sample to be investigated a reduced image of the focus situated within the beam of rays deflected by the said first deflecting mirror, while the said second focussing reflector arrangement forms an enlarged image of the said reduced focus at a distance before the said second deflecting mirror so that the beam of rays emitted by the said second deflecting mirror forms the prolongation of the beam of rays inciding upon the said first deflecting mirror just as if the auxiliary device did not exist.

IR spectrometers have been generally known before. They comprise an IR radiation source and a monochrometer or a two-beam interferometer for generating a measuring signal and optical means for focussing the said rays in a plane in which the sample to be investigated by transmission can be positioned by means of a sample holder. While the beam of rays starts diverging behind the focus, the straight section of the beam of rays which passes through the sample is directed via additional optical means towards a detector arrangement.

Many substances intended to be spectroscopically investigated in the IR range are, however, not pervious to IR radiation. For such substances it is, however, possible to make use of the IR radiation reflected and-/or diffused by their surface. IR spectrometry using diffuse radiation has been treated in "Analytical Chemistry", vol. 50 (1978), pages 1906 to 1910. The IR spectrometer described in this paper is especially designed for reflection measurements.

However, there exists a demand for auxiliary devices that can be used in normal IR spectrometers designed for carrying out transmission measurements, without the need of other modifications to the IR spectrometer. It is a precondition of any such solution that the convergent beam of rays normally directed upon the sample to be investigated by transmission must be allowed to enter such an auxiliary device unchanged and that after reflection by the sample the IR radiation must leave the device in the form of a divergent beam of rays taking exactly the position of the beam of rays that would normally be obtained after penetration of the sample. An auxiliary device of this type is marketed by the Harrick Scientific Corporation in Ossining, N.Y., U.S.A. The optical arrangements are provided in symmetry relative to a plane which when the auxiliary device is being used in the IR spectrometer is brought to coincide with the cross-sectional plane in which the beam of rays has a focus and in which the sample to be investigated by transmission is normally located. A first deflecting mirror directs the inciding beam of rays upon a deviating mirror arrranged laterally of the normally straight section of the beam of rays. The deviating mirror in turn directs the beam of rays upon an elliptical mirror which, for size considerations, is arranged on the opposite side, relative to the deviating mirror, of the straight section of the normally uninterrupted beam of rays. The elliptical mirror is formed by an ellipsoid section suited to form a reduced image of the focus of the original beam of rays which is normally located behind the first deflecting mirror, in a plane extending vertically to the cross-sectional plane in which the sample to be investigated by transmission is normally located. A second elliptical mirror receives the light reflected by the sample and directs it via a second deviating mirror which emits the IR radiation along the path which the original beam of rays would have taken. An enlarged image is projected on the surface of the sample at a point situated in front of the second deflecting mirror so that the beam of rays leaving the additional device seems to have a focus in the said cross-sectional plane intended to receive the sample to be investigated by transmission.

This known auxiliary device is, however, very costly since it uses elliptical reflectors the production of which requires extreme care because they are actually segments from an ellipsoid not centered relative to any ellipse axes. Further, the two elliptical reflectors, and the deflecting and deviating mirrors too, must be mutually adjusted with great care if the images of the focus planes are to coincide as desired and the beam of rays leaving the auxiliary device is to be a true prolongation of the beam of rays entering it. Further, it results from the symmetry of the arrangement that in the case of reflecting sample surfaces normally the specular reflection will be substantially caught. The specular reflection can be eliminated, to a certain degree, only by turning the sample, but this procedure will also flatten the path of the rays relative to the sample surface and, thus, impair the light output.

Further, Messrs. analect instruments in Irvine, Ca., U.S.A., also offer an auxiliary device of the type described comprising a reflector arrangement consisting of two paraboloid segments which have their openings oppositely directed and their focusses coincide. A beam of rays directed parallel to the plane in which the focus is located is reflected by one of the said parabolic reflectors into the focus plane while the other parabolic reflector emits the light reflected by the sample in the form of a parallel beam of rays in the same direction in which the parallel beam of rays incides upon the first reflector. This known arrangement also presents the disadvantage that two focussing reflectors must be adjusted so that their focusses coincide and that the reflected light is a virtual prolongation of the beam entering the device. To this end, the reflectors must be produced and mutually adjusted with great accuracy. In addition, this auxiliary device demands a parallel beam of rays which in the usual IR spectrometers does not exist in the area in which the sample to be investigated by transmission is normally arranged and which is available for the accommodation of the auxiliary device. So, the application of this known device requires modifications to such spectrometers, which may for instance consist in the removal of focussing reflectors and their replacement by deviating mirrors. Work of this type can, however, not be expected from the normal users of such spectrometers.

Now, it is the object of the present invention to provide an auxiliary device of the type described above which while being of simpler design as regards the production of its components and their adjustment, offers improved possibilities regarding the performance of various investigations.

According to the invention, this problem is solved in that each reflector arrangement comprises a collimator mirror for parallelizing the divergent beam of rays emitted by the associated deflecting mirror, and a section of a common parabolic mirror, the beams of rays emitted by the said collimator mirrors extending in parallel to the axis of the said parabolic mirror and the sample being arranged at a point coinciding with its focal point.

Accordingly, the auxiliary device of the invention does not use two separate focussing reflectors, but only a single axially symmetrical parabolic mirror whose focus is from the very beginning geometrically defined so that there is no need to adjust two reflectors to a common focus. At the same time, the sample can be arranged with great accuracy in the focus of the parabolic reflector. And the adjustment of the collimator mirror is also extremely simple as it must be ensured only that the parallel beam of rays extends in parallel to the axis of the parabolic reflector. The said collimator mirrors may also be used instead of the deviating mirrors of the known auxiliary device described before. This will already give a very compact structure. On the other hand, the reflector system of the auxiliary device according to the invention offers far greater freedom regarding the beam deflection as the only thing that matters is the generation of two parallel beams of rays inciding upon the parabolic mirror in parallel to its axis. This condition can be fulfilled in countless ways. In so far, the structure of the auxiliary device of the invention can be optimally adapted to any IR spectrometer available. Depending on the points where the parallel beams of rays incide upon the surface of the parabolic mirror, different positions, relative to the sample surface, are obtained for the beams of rays focussed on the sample. So, the angles at which the rays incide upon the sample and at which the rays directed to the measuring detector leave the sample can be varied by changing the said points of incidence. Consequently, any desired transitions from specular to diffuse reflection can be adjusted by such changes. The rays passing the focus may even form a straight beam of rays which would again permit the investigation of a sample by transmission and, thus, the use of the invention for micro transmission measurements. This possibility is of interest for the investigation of very small samples for which the beam of rays of the IR spectrometer is not sufficiently focussed.

To permit the before-mentioned variation of the points of incidence of the parallel beams of rays on the parabolic mirror, the parabolic mirror is in one embodiment of the invention displaceable in vertical direction relative to its axis and to the plane containing the axes of the parallel beams of rays. So, it is possible to shift the parallel beams of rays for instance from the corresponding diameter plane of the parabolic mirror into a plane extending in parallel thereto. In this manner, the angles of incidence of the rays upon a reflecting sample can be substantially changed. Besides, it is a requirement for transmission measurements that the parallel beams of rays lie in the diameter plane of the parabolic mirror.

Further, the parabolic mirror may be arranged for displacement in a direction vertical to its axis and parallel to the plane containing the axes of the parallel beams of rays. In this manner, different angles of incidence and emission can be adjusted, so that any desired transitions from specular to diffuse reflection, and vice versa, can be adjusted.

Another possibility to displace the parallel beam of rays relative to the parabolic mirror is obtained if at least one of the deflecting mirrors is arranged to pivot about an axis extending vertically to the axis of the inciding beam of rays and the plane containing the axes of the parallel beams of rays. Due to the fact that the deflecting mirrors are very close to the focus planes of the beams of rays, no negative effects of any importance will be produced by any such pivoting movement on the parallelization of the ray beam directed upon the parabolic mirror.

As mentioned before, a particular embodiment of the invention which may be realized by a corresponding adjustment of the displaceable elements, but may be made available also as a special auxiliary device, permits micro transmission measurements. In this embodiment of the invention, the axis of the parabolic mirror is arranged in one plane with the axes of the parallel beams of rays, the said axes are provided at a distance ensuring that they incide upon the parabolic mirror in the plane extending through the focus and vertically to the mirror axis, and the sample to be investigated by transmission is arranged in the focus.

As the collimator reflectors are intended to parallelize light arriving from a focus, they should, strictly speaking, also take the form of parabolic mirrors. Considering, however, that the angle of divergence of the beams of rays directed upon these collimator mirrors is only very small, it will generally suffice to use spherical mirrors as collimator reflectors.

To prevent direct light from the incoming beam of rays from passing by the side of the deflecting mirror and entering the outgoing beam of rays, a preferred embodiment of the invention has provided between the deflector mirrors a screen in substantially vertical arrangement relative to the straight section of the beam of rays. It is one of the advantages of the auxiliary device of the invention that the path of the rays permits the arrangement of such a screen without any detrimental effects on the path of the rays within the auxiliary device.

The parabolic mirror may have an opening provided in its center area, and a sample holder may project through the said opening. In this case it is easily possible to arrange, either on the parabolic mirror itself or on the mounting means for the mirror, stop means for the sample holder which ensure that the section of the sample holder carrying the sample comes to lie exactly in the focus of the parabolic mirror. The sample holder may have different designs, depending on whether the light is to be reflected by a face disposed vertically to the mirror axis or a face disposed in the mirror axis. Further, one could imagine sample holders permitting the insertion of a transparent sample disposed in the focus and vertically to that diameter plane of the parabolic mirror which contains the focus. And the sample holder may also be mounted to pivot about the axis of the parabolic mirror so that the angle formed between the surface of the sample and the incident and reflected beams of rays can be varied.

The invention will be described hereafter in detail with reference to the example shown in the drawings in which FIG. 1 shows a combined plan view and sectional view of an auxiliary device in accordance with the invention;

Figure 1:
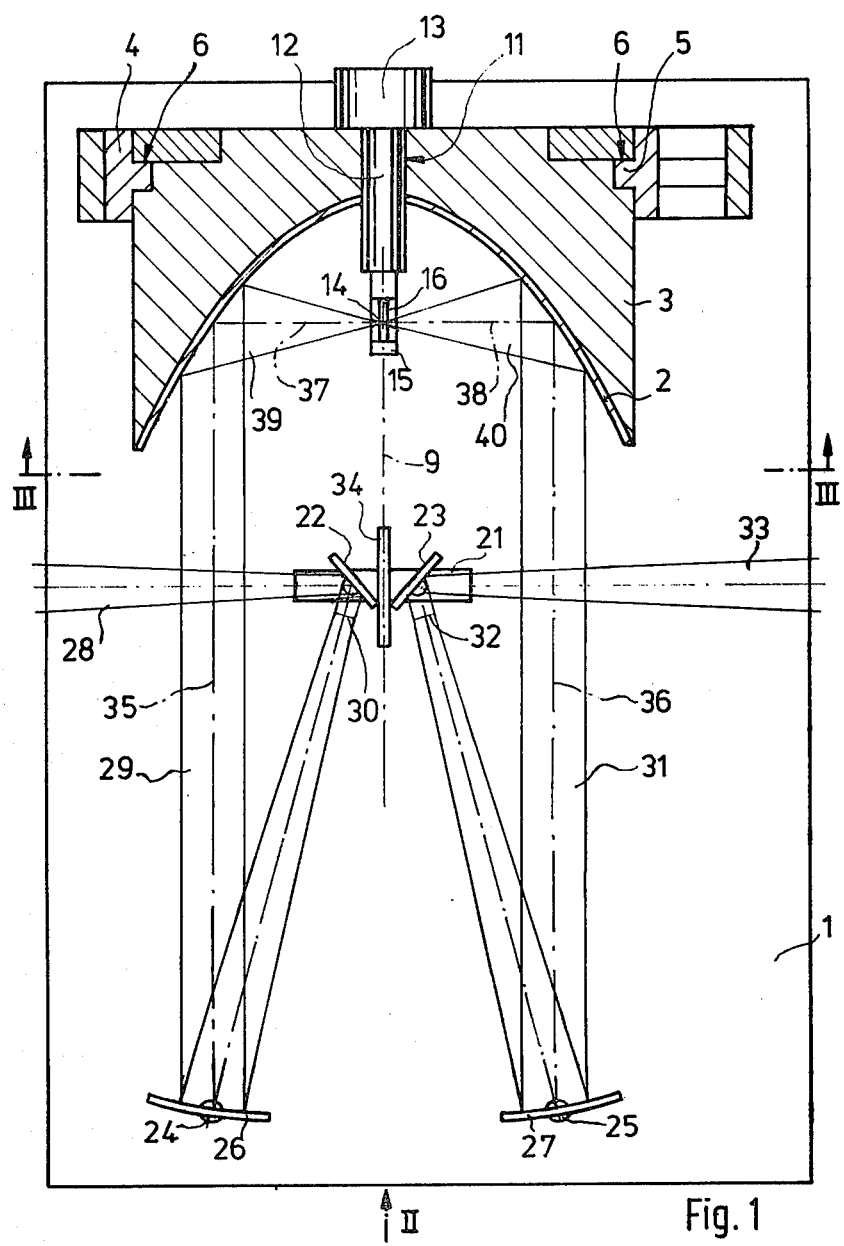
Figure 2:
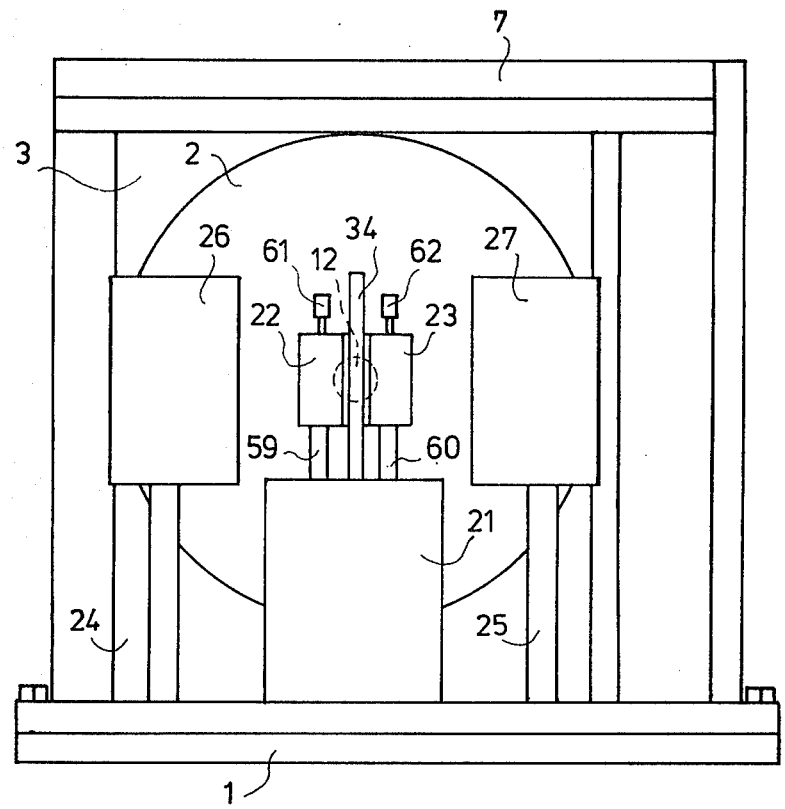
FIG. 2 is a view of the auxiliary device shown in FIG. 1, viewed in the direction of arrow II.
Figure 3:
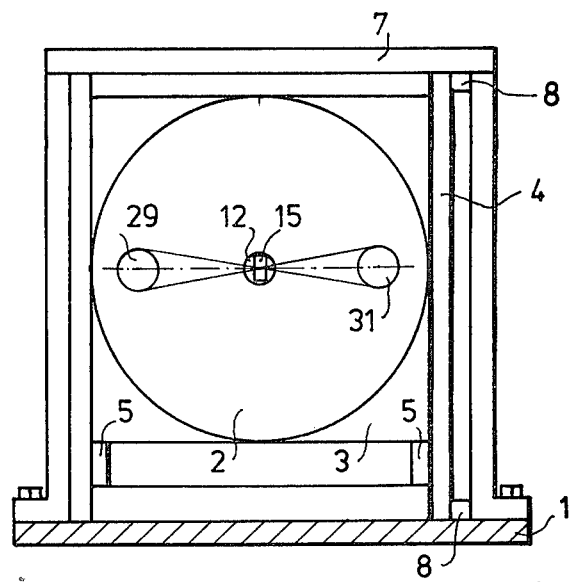
FIG. 3 is a section through the auxiliary device shown in FIG. 1 along line III—III, in reduced scale.

The auxiliary device for an IR spectrometer shown in FIGS. 1 to 3 comprises a base plate 1 carrying all optical means and permitting the installation of the auxiliary device as a compact unit into an IR spectrometer. The optical means comprise an axially symmetrical parabolic mirror 2 mounted on the front face of a mounting block 3. The mirror 2 may also be directly formed by the mirror-finished and perhaps coated front side of the mounting block 3. The mounting block 3 itself is mounted for vertical displacement in a frame 4. To this end, the vertical frame pieces are provided with ribs 5 engaging corresponding grooves 6 provided on the lateral faces of the mounting block 3. The frame 4 is mounted for horizontal displacement within a support 7 which in turn is fastened to the base plate 1 and has its horizontal legs equipped with webs 8 which engage corresponding grooves—not shown in the drawing—provided on the outsides of the horizontal frame pieces 4. Accordingly, the parabolic mirror 2 can be displaced in vertical direction within a plane extending vertically to its axis 9, and in parallel to base plate 1. For the purposes of the following description it shall be assumed that the auxiliary device is to be installed in an IR spectrometer with the base plate in horizontal position so that all planes and directions extending in parallel to the base plate will be defined as horizontal and all directions extending vertically thereto will be defined as vertical.

The block 3 is provided with a bore 11 arranged coaxially to the axis 9 of the parabolic mirror 2 and receiving a sample holder 12. The sample holder 12 comprises a cylindrical center portion fitting exactly into the bore 11. Its outer end is provided with a button-like section 13 of enlarged diameter by which the sample holder 12 can be easily gripped and which has its shoulder resting against the rear face of the mounting block 3. In this manner, the end of the sample holder 12 projecting into the parabolic mirror 2 is exactly positioned relative to the focal point 14 of the parabolic mirror 2. In the example shown in FIGS. 1 to 3, the inner end of the sample holder 12 carries a frame 15 with a sample 16 which is pervious to rays arranged therein and held in the focal point 14 in the vertical diameter plane of the parabolic mirror 2.

At a distance before the parabolic mirror 2, there are provided on the mounting plate 1 two deflecting mirrors 22, 23 mounted on a base 21 and, at a certain distance therefrom, two collimator deflectors 26, 27 mounted on columns 24, 25. The deflecting mirrors and collimator deflectors are arranged symmetrically relative to a vertical plane containing in the arrangement shown in FIG. 1 also the axis 9 of the parabolic mirror 2. The symmetrical arrangement is such that a convergent beam of rays 28 inciding upon the first deflecting mirror 22 in a direction vertical to the said vertical plane which in the absence of the deflecting mirror 22 would have a focus in the said vertical plane is deflected towards the said first collimator mirror 26 which in turn directs a parallel beam of rays 29 to the parabolic mirror 2. The collimator reflector 26 takes the form of a spherical mirror adjusted to ensure that its focus coincides with the focus 30 of the convergent beam of rays 28 which because of the presence of the deflecting mirror 22 is not positioned in the plane of symmetry of the arrangement, but directly behind the deflecting mirror 22, as shown in FIG. 1.

Due to the symmetrical arrangement, a parallel beam of rays 31 reflected by the surface of the parabolic mirror 2 in parallel to its axis 9 is focussed by the second collimator reflector 27 in a point closely before the second deflecting mirror 23 so that the divergent beam of rays 33 reflected by the second deflecting mirror 23 exhibits the same shape and divergence which the beam of rays 28 would have exhibited if the auxiliary device had not been present and the beam of rays 28 had been able to continue undisturbed along its straight path. Consequently, the auxiliary device can be used in an existing IR spectrometer without any change to its beam generation and detection means. In order to prevent any trouble that might be encountered in the use of the auxiliary device due to rays passing directly from the incoming beam of rays 28 into the outgoing beam of rays 33, a screen 34 is arranged between the deflecting mirrors 22, 23 in the vertical axis of symmetry of the optical arrangement described.

It is an inherent property of parabolic reflectors that incoming beams of rays are focussed in their focal point while beams of rays emitted from their focal point are reflected by the mirror surface in the form of a parallel beam of rays. Due to the different radii of curvature and/or the different distances between the focus planes and the mirror surfaces, the focus obtained in the focal point 14 is considerably smaller than the focus 30 of the incoming beam of rays 28 so that the auxiliary device is also suited for investigating very small samples. The auxiliary device of the invention can therefore also be designated as "micro-focussing unit". The unit permits measurements by transmission just as IR spectrometers without such auxiliary devices. It is a precondition for measurements by transmission that, as shown in FIGS. 1 to 3, the parallel beams of rays 29 and 31 inciding upon the parabolic mirror 2 must lie within a common diameter plane so that the radiation penetrating through the sample 16 will be directed as completely as possible towards the collimator reflector 27 provided on the output side. In a particularly convenient arrangement, the axes 35 and 36 of the parallel beams of rays 29 and 31 incide upon the parabolic mirror 2 of a point in which the cross-sectional plane of the parabolic mirror 2 passing through the focal point intersects the surface of the parabolic mirror because in this case the axes 37, 38 of the beams of rays 39 and 40 directed towards or away from the focal point will vertically pass through the diameter plane containing the sample 16 and, thus, through the sample itself.

Figure 4:
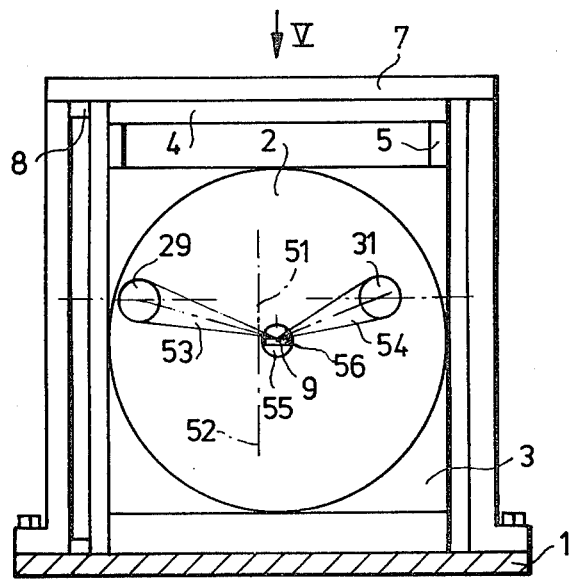
FIG. 4 is a section similar to that shown in FIG. 3, but with displaced parabolic mirror.
Figure 5:
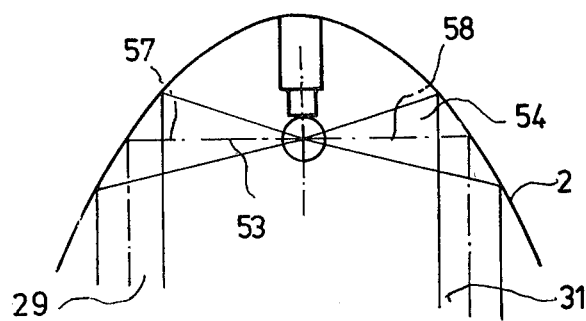
FIG. 5 is a diagrammatic representation of the rays inciding upon the parabolic mirror of the arrangement shown in FIG. 4, viewed in the direction of arrow V.
Figure 6:
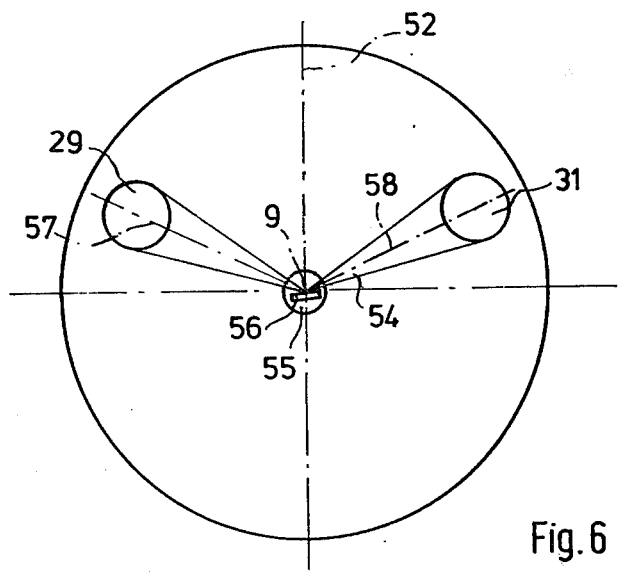
FIG. 6 is a diagrammatic representation similar to that of FIG. 4, but with parallel beams of rays extending in parallel to a diameter plane of the parabolic mirror and a sample tilted relative to the same plane.

As has been mentioned before, the auxiliary device is, however, not primarily intended for use in microtransmission measurements, but mainly for use in reflection measurements. The transition from transmission measurements in accordance with FIG. 3 to reflection measurements can be achieved simply by displacing the parabolic reflector in a plane vertical to its axis. As can be seen in FIG. 3, when used for micro-transmission measurements the frame 4 occupies the left-hand position in the support 7 and the mounting block 3 with the parabolic mirror 2 are in their upper position in frame 4. By displacing the mounting block 3 in frame 4 in downward direction and the frame in support 7 to the right, one obtains the position shown in FIG. 4 in which the parallel beams of rays 29, 31 still extend in parallel to the axis of the parabolic mirror 2, but this in a horizontal plane 51 situated above the axis 9 of the parabolic mirror. In addition, the axis 9 of the parabolic mirror 2 is laterally set off against the vertical plane of symmetry 51 for the two beams of rays 29, 31. From this it results that starting from the mirror axis 9 the beams of rays 53, 54 are upwardly directed between the focal point and the parallel beams of rays 29, 30, at different angles relative to the vertical line. Now, if a sample is placed in the focal point of the parabolic mirror 2 by means of a sample holder 55 provided with a shoulder 56 on which a sample can be mounted so that one horizontal surface of the sample comes to lie in the area of the focal point, the introduced radiation incides at an angle upon this surface and is reflected by it at a corresponding angle. Due to the different angles relative to the vertical line, the radiation which is directly reflected at the angle of incidence does not enter the area of the beam of rays 54 from which the beam of rays 31 inciding upon the deviating mirror 27 is formed. The area of the beam of rays 54 is entered only by the diffuse reflection from the sample. Further, due to the different distances of the beams of rays 29 and 31 from the vertical diameter plane of the parabolic mirror 2, the axes 56 and 57 of the beams of rays 53 and 54 are no longer aligned when projected into the horizontal plane, as shown in FIG. 5, so that for this reason, too, the directly reflected radiation is no longer picked up.

It can be easily seen that a displacement of the parabolic mirror 2 from the position shown in FIG. 3 in downward direction only leads to a symmetrical arrangement of the beams of rays 29 and 31 relative to the vertical plane 52 passing through the mirror axis 9. In this position, a substantial amount of radiation directly reflected by the sample would get into the outgoing beam of rays 54 if the sample holder with its shoulder 56 were oriented as shown in FIG. 4. However, the specular reflexion can be avoided in this case by turning the sample holder 55 around its axis which coincides with the mirror axis 9 until the surface of the sample mounted on the shoulder 56 forms an angle with the horizontal plane and, accordingly, the angles formed between the axes 57 and 58 and the surface of the sample are different again. It results that any desired ratio of specular and diffuse reflexion, from purely specular reflexion to purely diffuse reflexion, can be adjusted simply by turning the sample about the mirror axis.

It should also be noted that the position of the parallel beams of rays 29 and 31 relative to the parabolic mirror 2 may be varied by turning the associated deflecting mirror 22 or 23 about a vertical axis. To this end, the deflecting mirrors 22, 23 are mounted in the base 21 by means of rods 59, 60 rotatably seated in the base 21.

Buttons 61 and 62 arranged on the upper edge of the mirrors 22, 23 facilitate the turning motion. Likewise, the columns 24, 25 carrying the collimator reflectors 26, 27 may be designed to enable the collimator reflectors to be tilted for adjustment purposes.

It goes without saying that the invention is not restricted to the example shown in the drawing, but that various deviations are possible without departing from the scope of the invention. This applies in particular to the mechanical structure of the device which may take any desired form. The described adjusting mechanisms may, for instance, be provided only in part, except for the necessary setting means for the individual components. Where adjusting mechanisms are provided they may either have two or more pre-determined, for instance stop-defined, positions or be continuously variable. Considering that in the auxiliary device of the invention the image of the focus is formed with the aid of an intermediate parallel beam of rays the length of which is absolutely uncritical, the total structure of the optical system need not necessarily be symmetrical as parallel beams of rays of different lengths remain without any influence which makes it possible to give the device a design in which the optic paths of the beam inciding upon the sample and the beam emitted from the sample have different lengths. Accordingly, one could, for instance, envisage to create an arrangement with the aid of deviating mirrors in which the axis of the parabolic mirror extends in parallel to the direction of the beam of rays in the IR spectrometer. So, in the aggregate, a great number of variations are possible which represents a particular advantage of the auxiliary device of the invention.

We claim:

1. An auxiliary device for carrying out reflection measurements using an IR spectrometer designed for the performance of transmission measurements and comprising optical means for generating a beam of rays focussed in a cross-sectional plane located within a straight section and intended to receive the sample to be investigated by transmission, which auxiliary device comprises two deflecting mirrors to be positioned in the straight beam section on both sides of the cross-sectional plane and further two focussing reflector arrangements of which the first forms at the location of the sample to be investigated a reduced image of the focus situated within the beam of rays deflected by the said first deflecting mirror, while the said second focussing reflector arrangement forms an enlarged image of the said reduced focus at a distance before the said second deflecting mirror so that the beam of rays emitted by the said second deflecting mirror forms the prolongation of the beam of rays inciding upon the said first deflecting mirror just as if the auxiliary device did not exist, characterized in that each reflector arrangement comprises a collimator mirror (26, 27) for parallelizing the divergent beam of rays emitted by the associated deflecting mirror (22, 23), and a section of a common parabolic mirror (2), the beams of rays (29, 31) emitted by the said collimator mirrors (26, 27) extending in parallel to the axis (9) of the said parabolic mirror (2) and the sample (16) being arranged at a point coinciding with its focal point (14).

2. An auxiliary device in accordance with claim 1, characterized in that the parabolic mirror (2) is mounted for displacement in a direction extending vertically to its axis (9) and to the plane containing the axes (35, 36) of the parallel beams of rays.

3. An auxiliary device in accordance with claim 1 or 2, characterized in that the parabolic mirror (2) is mounted for displacement in a direction vertical to its axis (9) and parallel to the plane containing the axes (35, 36) of the parallel beams of rays.

4. An auxiliary device in accordance with claim 1 or 2, characterized in that at least one of the deflecting mirrors (22, 23) is mounted to pivot about an axis extending vertically to the axis of the inciding beams of rays (28, 33) and the plane containing the axes (35, 36) of the parallel beams of rays.

5. An auxiliary device in accordance with claim 1 or 2, characterized in that the axis (9) of the parabolic mirror (2) lies in the same plane as the axes (35, 36) of the parallel beams of rays, that the distance between the axes is such that their point of intersection with the parabolic mirror (2) lies in the plane passing the focal point (14) and extending vertically to the mirror axis (9) and that a sample (16) intended for being investigated by transmission is arranged in the focal point (14).

6. An auxiliary device in accordance with claim 1 or 2, characterized in that the collimator mirrors (26, 27) and the parabolic mirror (2) are arranged on opposite sides of the straight section of the beam of rays (28, 33).

7. An auxiliary device in accordance with claim 1 or 2, characterized in that the collimator mirrors (26, 27) take the form of spherical mirrors.

8. An auxiliary device in accordance with claim 1 or 2, characterized in that there is arranged between the deflecting mirrors (22, 23) a screen (34) extending substantially vertically to the straight section of the beam of rays (28, 33).

9. An auxiliary device in accordance with claim 1 or 2, characterized in that the parabolic mirror (2) has an opening (11) in its central area for receiving a sample holder (12).

10. An auxiliary device in accordance with claim 9, characterized in that the sample holder (12) is mounted to pivot about the axis of the parabolic mirror (2).

* * * * *